US00PP08863P

United States Patent [19]

Oda et al.

[11] Patent Number: Plant 8,863

[45] Date of Patent: Aug. 16, 1994

[54] PINEAPPLE PLANT NAMED 'CO-2'

[75] Inventors: Calvin H. Oda, Honolulu, Hi.; David D. F. Williams, Fort Collins, Colo.

[73] Assignee: Del Monte Fresh Produce N.A., Inc., Coral Gables, Fla.

[21] Appl. No.: 110,808

[22] Filed: Aug. 23, 1993

[51] Int. Cl.[5] ..... A01H 5/00

[52] U.S. Cl. ..... Plt./33.1

[58] Field of Search ..... Plt. 33.1, 88.8, 100

[56] References Cited

U.S. PATENT DOCUMENTS

*Primary Examiner*—James R. Feyrer

*Attorney, Agent, or Firm*—Fitzpatrick, Cella, Harper & Scinto

[57] ABSTRACT

A new plant variety of the Bromeliaceae, or pineapple, family, *Ananas comosus*, has been developed as an interspecific cross between Pineapple Research Institute hybrid clone 58-1184 and Pineapple Research Institute (PRI) hybrid clone 59-443, and has been named hybrid CO-2. This hybrid clone generally resembles the parent varieties, but is distinguished therefrom in that this plant produces a sweeter, more viamin C rich fruit, which is low in parasitic fruit diseases, and tolerant or resistant to the physiological disorder called internal browning. This plant has more uniform yellow color, good fruit appearance after refrigerated storage, and produces acceptable crop yields of saleable fresh pineapple.

3 Drawing Sheets

BACKGROUND AND SUMMARY OF THE INVENTION

The invention relates to a new and distinct plant variety of the Bromeliaceae or pineapple family and which was derived from the cross of Pineapple Research Institute of Hawaii hybrid clone 58-1184 and Pineapple Research Institute (PRI) hybrid clone 59-443 and has been named hybrid clone CO-2 by the inventors.

The specimen was under cultivation in a nursery at Del Monte Fresh Produce (Hawaii) Inc. at the time of discovery and since then, the new variety has been asexually reproduced at the same nursery by the propagation of stem cuttings and use of vegetative parts of the plants taken from the specimen.

Smooth Cayenne pineapple (*Ananas comosus* (L. mer)) is the principal commercial pineapple variety grown in Hawaii and in other pineapple growing areas throughout the world. Hybrid clones are related to Smooth Cayenne pineapple containing more than 50 percent Smooth Cayenne genes but were altered using cross pollination methods.

The PRI hybrid clone 58-1184 of the genus Ananas is a pineapple variety developed by the Pineapple Research Institute Hawaii. Hybrid clone 58-1184 can be characterized by its short leaves, with light green color and reddish-brown leaf margins. Leaf shape is typical of Smooth Cayenne pineapple, however, hybrid clone 58-1184 has slightly spiny or thorny leaf margins. Plant vigor and the length of vegetative and fruiting cycles is similar to Smooth Cayenne pineapple. Hybrid clone 58-1184 produces small, alightly round fruit on short plants. Crop yields may be as much as 30 percent lower than Smooth Cayenne pineapple. This variety is noted for high incidence of the fungal fruit disease called Fruitlet Core Rot, but is tolerant to the physiological disorder, Internal Browning. The edible flesh of the fruit is sweet, moderately yellow, with lower total acid levels than Smooth Cayenne pineapple.

The hybrid clone 59-443 of the genus Ananas is a pineapple variety developed by the Pineapple Research Institute at Wahiawa, Hawaii. It is distinguished from Smooth Cayenne pineapple by its dark green leaf color and reddish to reddish-brown leaf margins. Leaf shape is narrower than, leaf length similar to, and leaf texture more rigid than Smooth Cayenne pineapple. This variety grows rapidly, maturing one month faster than Smooth Cayenne clones. Crop yields may be slightly lower than Smooth Cayenne pineapple. Hybrid clone 59-443 is more susceptible than Smooth Cayenne clones to the plant diseases caused by *Phytophthora cinnamomi* and *Phytophthora parasitica*. It is tolerant to the physiological fruit disorder, internal browning. The fruit is square shouldered, with large, flat fruitlets. The edible flesh of the fruit is porous, more yellow, and sweeter than Smooth Cayenne pinepple.

The general objective of this invention has been to develop a new variety of pineapple that produces a sweeter, more vitamin C rich fruit, is less prone to parasitic fruit diseases, more tolerant or resistant to the physiological disorder called internal browning, and having more uniform yellow color, and good fruit appearance after refrigerated storage. Other objectives of this invention were to develop a new variety that was tolerant to pineapple plant diseases, and which produces acceptable crop yields of saleable fresh pineapple.

These objectives have been fully realized by the development of the new plant variety described here in detail. The new plant variety was developed at the Pineapple Research Institute at Wahiawa, Hi as a hybrid clone secured by cross pollinating a flower of hybrid clone 58-1184 with pollen taken from a plant of hybrid clone 59-443. The seeds taken from the ovaries of the material variety were cultivated at the Pineapple Research Institute. After prolonged observation of the seedlings, the hybridized plant was selected and asexually reproduced by the inventors at the Pineapple Research Institute through propagation of stem cuttings and use of vegetative parts of the original hybrid plant.

Through successive propagations, the inventors have ascetained that specimens of the new plant variety generally resemble the parent varieties but are distinguishable from both parents as well as other varieties of pineapple known to the inventors in that the new variety has greater sugar and higher vitamin C content, distinctive mixed tropical flavor, greater pigmentation and fiber content of the edible flesh, higher resistance to internal browning development, and good crown and shell appearance following refrigerated storage.

BRIEF DESCRIPTION OF THE VARIOUS VIEWS OF THE DRAWINGS

The accompanying drawings serve, by color photographic means, to illustrate the new plant variety through the depiction of typical specimens of the new pineapple variety at anthesis, as true as reasonably possible. In particular, FIGS. 1–5 provided various views of the present invention:

FIG. 1 shows a number of plants of the present variety, while

Figure 1:
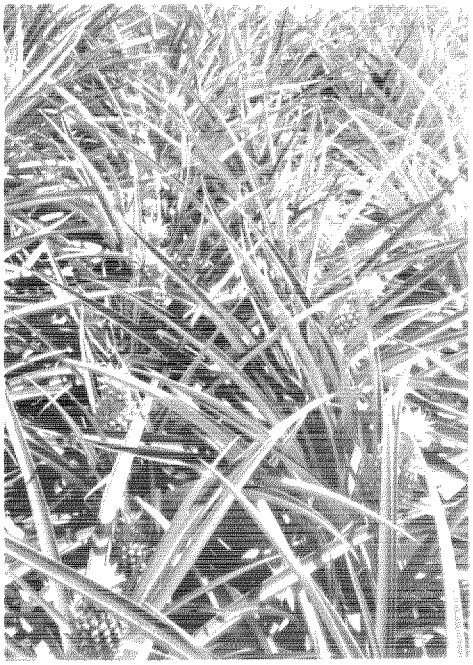
Figure 2:
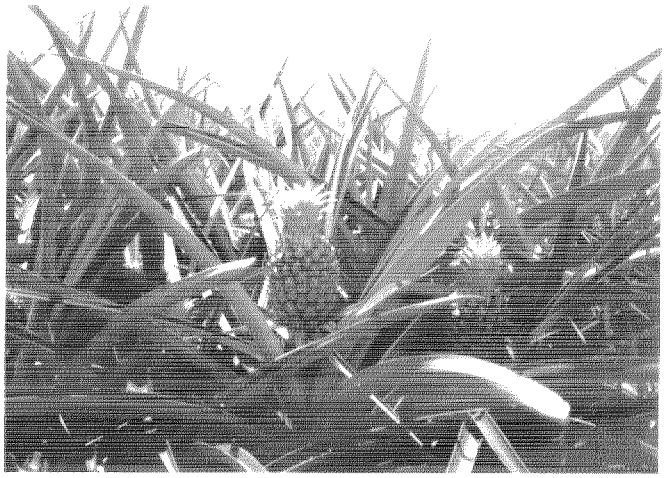
FIGS. 2–4 are close-up views of a single pineapple fruit.
Figure 3:
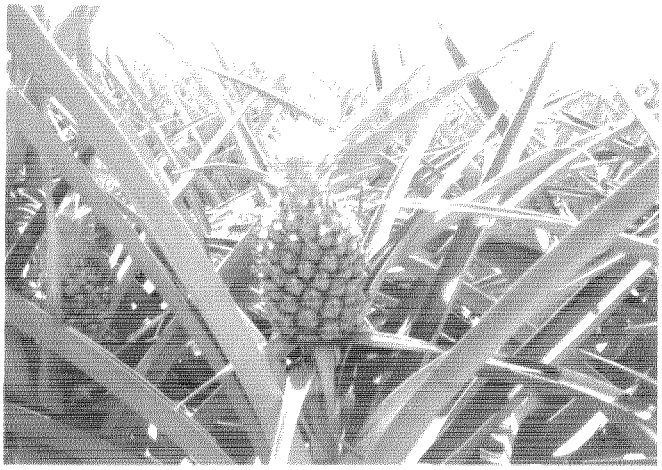
Figure 4:
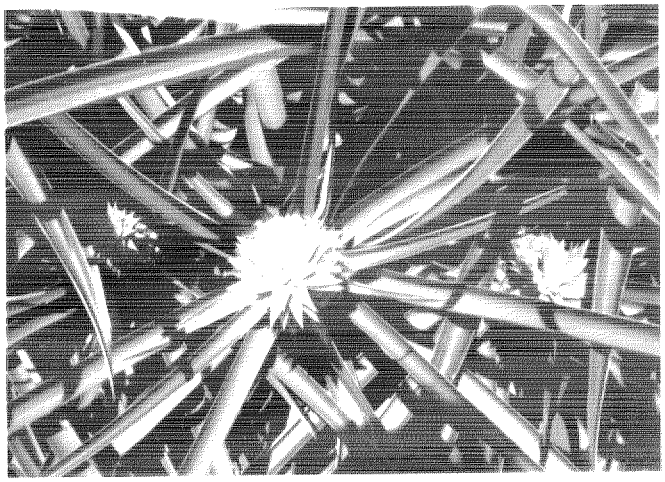
Figure 5:
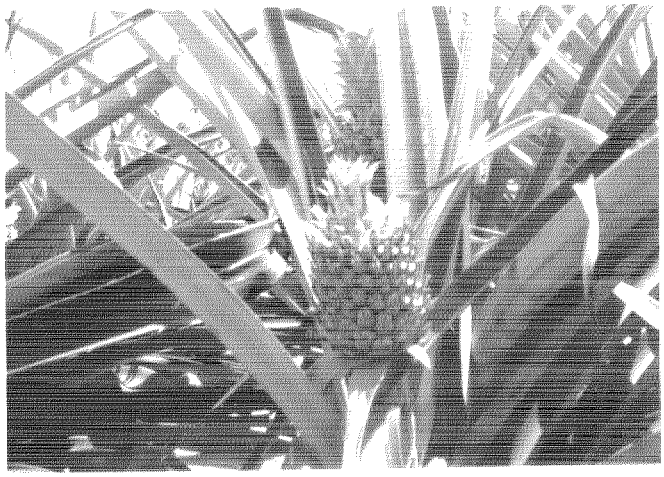
FIG. 5 shows in close-up an immature fruit.

The following detailed descriptions of the new plant variety are based on observations of well fertilized specimens which were grown in the central Oahu Plain on the island of Oahu in Hawaii under field conditions and where temperature generally range from about 15.5° C. to 27.0° C. during the winter months and from about 21.0° C. to 32.0° C. during the summer months.

Except where general terms of ordinary dictionary significance are obviously used, color terminology and color designations reported herein are in accord with the method described in the United States Department of Commerce, National Bureau of Standards, Publication 265, 225 entitled "The Universal Color Language and Color Names Dictionary" with the color designations having been derived from interpretations of Munsell Color Notations obtained by comparing plant specimens with color specimens in the current "Munsell Student Set" published by Munsell Color Macbeth, a division of Kollmorgen Corporation, Newburgh, N.Y. and to which the reported notations (Munsell Hue, Munsell Value/Munsell Chromas) are referenced.

The following is a description of the general population of the new variety grown at Del Monte Fresh Produce (Hawaii) Inc. at Kunia, Oahu, in the State of Hawaii from vegetative parts of the new pineapple plant, the description having been taken during the period of inflorescence development in the month of May 1993.

DETAILED PLANT DESCRIPTION

Name: *Ananas comosus* var. 'CO-2'.

Parentage:

I. *Seed parent.*—Hybrid Clone 58-1184.

II. *Pollen parent.*—Hybrid Clone 59-443.

Origin: A cross between PRI hybrid clones 58-1184 and 59-443.

Classification:

I. *Botanic.*—Bromeliaceae or pineapple family. Subfamily: Bromelioideae. Genus: Ananas. Subgenus: *comosus. Species:* 58-1184×59-443 (var CO-2).

II. *Commercial.*—Bromeliad fruit plant.

Form: Terrestrial (in cultivation), with overlapping sessile leaves from a funnel-formed rosette surrounding a composite influorescence (during anthesis) and forming 2 to 3 rootable offshoots (slips) that initiate during or subsequent to anthesis, and dominant offshoots (or fruiting suckers) that produce subsequent crops after initial fruit harvest.

Stems:

I. *General.*—Short, upright and sheathed by overlapping leaves, each leaf axil having a dormant axillary bud.

II. *Stem texture.*—Glabrous and fleshy.

III. *Stem size.*—A) Length (above soil level): Usually between 24 and 32 cm at anthesis. B) Diameter between 22 to 26 cm at soil level at anthesis.

IV. *Stem shape.*—Terete and tapered somewhat to a narrower diameter at soil level.

Leaves:

I. *General.*—Closely overlapping sessile leaves (formed in acropetal succession) forming a dense rosette, the outline of which in longitudinal section is roughly heart shaped. The leaves 40 to 70 in number, have 5/13 phyllotaxy.

II. *Leaf texture.*—A) Upper epidermal area: Glabrous, semi-rigid and channelled (or concave) in the upper epidermal area (except at the leaf tip). B) Lower epidermal area: Finely striated (longitudinally) and appears covered with white furfuraceous layer consisting of scale-like trichomes.

III. *Leaf arrangement.*—Alternate and rosulate.

IV. *Leaf margins.*—Plane, with rarely found irregularly spaced small deltoid-cuspidate hooked spines that are usually located on the lower portions of leaves. Leaf margins are very smooth in comparison to other Smooth Cayenne varieties.

V. *Leaf venation.*—Parallel and obscure.

VI. *Leaf shape.*—Leaves are not uniform in shape and varies with the position of the leaf on the stem. The basal or oldest leaves, are lanceoate in form while the base is considerable expanded. There is a decided narrowing in width between non-chlorophyllous (basal) and chlorophyllous (or main portion) of the leaves. The longest or most mature leaves, are lanceolate in form, but the base is without the arcuate expansions of the preceding leaves. The remaining leaves (or center leaves of the plant rosette) are lanceolate in form with no expansion of width into a distinct base.

VII. *Leaf size (at anthesis).*—A) Length: Usually between 77 and 110 cm for those leaves originating from the medium part of the stem with the nonchlorophyllous base usually being 4.5 and 5.7 cm in length. B) Width: Usually between 6.0 and 6.5 cm at the midleaf area of the longest leaves. The expanded basal disk usually has a maximum width of 9.5 to 10.8 cm. C) Thickness: In the longest leaves, usually 2.2 to 2.9 mm at the center of the midleaf area and tapering laterally to 1.7 to 1.8 mm at the margins while becoming slightly thinner at the tip. The expanded basal disk at the midstem area usually has a maximum thickness of 3.1 to 4.1 cm at the center of the blade and tapering laterally to 1.6 to 2.2 mm at the margins.

VII. *Color.*—A) Upper epideral surface: 1. General: Color is usually dominated by yellowish green, olive green, and reddish green hue that merges with color in the leaf tip dominated by reddish green to reddish brown hue. The field of the basal disk area is, in color, dominated by greenish yellow and light green hue. 2. Achlorophyllous basal disk area: Commonly light green yellow (5GY 8/4). 3. Midleaf Area: Commonly olive gray (near 5.0Y 8/4), (5.0Y 7/6), greyish olive (5.0GY 6/4), (5.0 GY 5/4), (5.0GY 5/6), reddish brown (5.0YR 4/2), and reddish purple (5.0 RP 4/2). 4. Leaf tip area: Commonly greyish olive (5.0GY 6/4), 5.0 GY 5/4), yellow green (near 5.0Y 8/8), reddish brown (5.0YR 6/4), and/or reddish purple (5.0RP 4/2), (5.0RP 4/2). B) Lower epidermal area: 1. General: Commonly olive green to greyish oliver green with pale white basal disk area. 2. Lower epidermal surface: Scurfy surface that obscures colors which are commonly olive green (5.0GY 8/4), (5.0GY 7/6) and/or greyish olive green (5.0GY 7/2), (5.0GY 6/2).

Inflorescence:

I. *General.*—Composite flower with 90 to 135 fruitlets per inflorescence borne of a long peduncle approximately 21.6 cm in length at the apical meristem. Individual bi-sexual flowers consists of three sepals, six stamens, three (3) stigmas, and three (3) carpels. The inflorescence is self incompatible producing edible fruit parthenocarpically.

II. *Texture.*—Glabrous and fleshy.

III. *Shape.*—Oval with slightly raised flowers with distinctive reddish geen crown. Crown leaves are short and erect at anthesis.

IV. *Size and color.*—Comparable to specimens of *Ananas comosus* L. mer.

Fruit:

I. *Fruit size.*—Usually 2.86 lbs. to 5.71 lbs. in weight with average fruit weight of 4.54 lbs. at the first harvest. Produce 4 to 37 percent higher crop yields (tons/acre) than Smooth Cayenne.

II. *Fruit shape.*—Square shouldered fruit with large flat fruitlets. Large, crown with narrow semi-rigid leaves.

III. *How borne.*—Fruit develop from the apical meristem of the plant on a long peduncle, usually 23 to 25 cm in length.

IV. *Plant disease resistance.*—Slightly more susceptible than Smooth Cayenne to *Phytophthora cinnamomi* and *Phytophthora parasitica.*

V. *Taste test records.*—Taste tests at nursery indicated 65 percent of group like the appearance of the flesh and 77 percent like the taste.

VI. *Color.*—A) Fruit shell: Commonly darkish green (5.0G 5/4), (5.0G 4/4), (5.0 ¾), olive green (5.0GY 7/6), (5.0GY 6/6), (5.0GY 5/6), and/or golden yellow (5.0Y 8/10, 5.0Y 8/12). B) Edible flesh: Commonly pale yellow (nearly 5.0Y 8/6), (5.0Y 8/8) and/or golden yellow (5.0Y 8/10), (5.0Y 8/12).

VII. *Brix level.*—Typically 15.0 to 16.7 degrees.

VIII. *Total acid levels.*—Typically 0.42 to 0.91 gms critric acid/100 milliliters.

IX. *Vitamin C content.*—Usually 30.8 to 55.5 mg/100 ml (or approximately 3 to 4 times higher than Smooth Cayenne pineapple).

The following is a general description of the new plant variety that was grown from the propagation of a vegetative offshoot in a nursery at Del Monte Fresh Produce (Hawaii) Inc. at Kunia, Oahu, Hi.

Age of plant: 12 months from initial propagation Diameter of plant: About 164 cm between opposite leaf tips at midpoint.

Height of plant: 107 cm above ground surface.

Stem:

I) *Length.*—33 cm

II) *Diameter.*—About 24 cm at base.

Leaves:

I) *Number.*—43.

II) *Length*—103 cm at longest leaves.

III) *Width (largest leaves).*—At midleaf (max): 5.1 cm; at basal disk area (max): 10.2 cm.

IV) *Thickness:* about 2.9 mm along the axis.

V) *Color.*—A) Upper epidermal area — chlorophyllous area: Commonly greyish olive (5.0GY 7/4), (5.0GY 6/4), (5.0GY 5.4), olive grey (5.06/4), 5.0Y 5/4), (5.0Y 4/4), and/or reddish brown (5.0R 6/4), 5.0R 5/4, (5.0R 4/4).B) Upper epidermal area—non-chlorophyllous area: Commonly pale white to light green (5.0G 8/2). C) Lower epidermal area: Commonly olive green (5.0GY 8/4), (5.0GY 7/6), 5.0GY 6/8, and/or greyish green (5.0GY 7/2), (5.0GY 6/2).

Inflorescence: Lacking.

What we claim is:

1. The new and distinct variety of Pinapple Plant substantially was shown and described herein.

* * * * *

Disclaimer

PP 8,863—Calvin H. Oda, Honolulu, HI; David D.F. Williams, Fort Collins, CO. PINEAPPLE PLANT NAMED 'CO-2'. Patent dated August 16, 1994. Disclaimer filed March 13, 2003, by the assignee, Del Monte Fresh Produce N.A., Inc.

Hereby disclaim the complete claim in the above-identified patent (claim 1).

*(Official Gazette, July 26, 2005)*